US012736548B2

(12) United States Patent
Kitajima

(10) Patent No.: US 12,736,548 B2
(45) Date of Patent: Sep. 15, 2026

(54) METHOD FOR STABILIZING HEMOGLOBIN

(71) Applicant: ARKRAY, Inc., Kyoto (JP)

(72) Inventor: Yukie Kitajima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 560 days.

(21) Appl. No.: 18/343,428

(22) Filed: Jun. 28, 2023

(65) Prior Publication Data

US 2024/0003919 A1 Jan. 4, 2024

(30) Foreign Application Priority Data

Jun. 29, 2022 (JP) ................................ 2022-105015

(51) Int. Cl.
*G01N 33/72* (2006.01)

(52) U.S. Cl.
CPC ..... *G01N 33/721* (2013.01); *G01N 2333/805* (2013.01); *G01N 2496/00* (2013.01)

(58) Field of Classification Search
CPC ........... G01N 33/721; G01N 2333/805; G01N 2496/00; G01N 1/38; G01N 2001/2893; C07K 14/805
USPC ............................................................ 436/66
See application file for complete search history.

(56) References Cited

U.S. PATENT DOCUMENTS

| | | | | |
|---|---|---|---|---|
| 4,172,049 | A | 10/1979 | Pfeil et al. | |
| 4,372,747 | A * | 2/1983 | Gabbay | G01N 33/723 436/67 |
| 2009/0137612 | A1 | 5/2009 | Waugh | |

FOREIGN PATENT DOCUMENTS

| | | | |
|---|---|---|---|
| JP | S53-141696 | A | 12/1978 |
| JP | H01-309687 | A | 12/1989 |
| JP | 2000-319238 | A | 11/2000 |
| JP | 2003-14768 | A | 1/2003 |
| JP | 2014-174057 | A | 9/2014 |
| JP | 2016-519311 | A | 6/2016 |
| JP | 6514190 | B2 | 5/2019 |
| WO | 2014/182666 | A1 | 11/2014 |

OTHER PUBLICATIONS

Miike, High-Sensitivity Measurement Method and Reagent for Hemoglobin, English Abstract, Sep. 22, 2014, p. 1, obtained on Dec. 18, 2025. (Year: 2014).*

Chris E. Cooper et al., "Peroxidase activity of hemoglobin towards ascorbate and urate: A synergistic protective strategy against toxicity of Hemoglobin-Based Oxygen Carriers (HBOC)", Biochimica et Biophysica Acta, vol. 1784 (2008), pp. 1415-1420, Apr. 16, 2008.

Annelie Pichert et al., "Interaction of the chlorite-based drug WF10 and chlorite with hemoglobin, methemoglobin and ferryl hemoglobin", Archives of Biochemistry and Biophysics, vol. 585 (2015), pp. 82-89, Sep. 21, 2015.

Thao Yang et al., "The effect of crosslinking by bis(3,5-dibromosalicyl) fumarate on the autoxidation of hemoglobin", Biochemical and Biophysical Research Communications, vol. 163, No. 2 (1989), pp. 733-738, Sep. 15, 1989.

Magdalena Makarska-Bialokoz, "Analysis of the binding interaction in uric acid-Human hemoglobin system by spectroscopic techniques", Spectrochimica Acta Part A: Molecular and Biomolecular Spectroscopy, vol. 178 (2017), pp. 47-54, Jan. 31, 2017.

The extended European search report issued by the European Patent Office on Oct. 13, 2023, which corresponds to European Patent Application No. 23182210.7-1111 and is related to U.S. Appl. No. 18/343,428.

Communication pursuant to Article 94(3) EPC issued by the European Patent Office on Sep. 3, 2025, which corresponds to European Patent Application No. 23 182 210.7-1111 and is related to U.S. Appl. No. 18/343,428.

* cited by examiner

*Primary Examiner* — Christine T Mui
(74) *Attorney, Agent, or Firm* — Studebaker Brackett PLLC

(57) ABSTRACT

A method that is capable of stably preserving hemoglobin in a solution. A method for stabilizing hemoglobin in a solution includes causing at least one of acetylacetone or uric acid to coexist in the solution containing hemoglobin.

20 Claims, 1 Drawing Sheet

METHOD FOR STABILIZING HEMOGLOBIN

CROSS-REFERENCE TO RELATED APPLICATION

This application claims benefit of priority to Japanese Patent Application No. 2022-105015, filed Jun. 29, 2022, the entire content of which is incorporated herein by reference.

BACKGROUND

Technical Field

The present disclosure relates to a method for stabilizing hemoglobin in a solution.

Background Art

A measured value obtained in a laboratory test carried out on a biological specimen is an important indicator that relates to the determination of a health condition, as well as the diagnosis and treatment of a disease. To reliably determine a measured value, therefore, quality control of the test system is required. A control reagent that contains substances that are identical to components in a biological specimen or that are suspected to be such substances is utilized as a control reagent for precision management. In addition, the control reagent is required to be a highly-stable reagent having small changes over time, and a scheme to realize such stabilization has been examined as described, for example, in Japanese Patent No. 6514190, and JP-A-2003-14768. Japanese Patent No. 6514190 discloses a kit for quality control in which, of substances to be measured in urine, unstable substances are lyophilized, and stable substances are preserved in a solution. JP-A-2003-14768 discloses the utilization of 2-ketoglutaric acid or the like for the stabilization of hemoglobin.

SUMMARY

The present disclosure provides a novel method that is capable of stably preserving hemoglobin in a solution, use of a hemoglobin solution in a method for measuring hemoglobin in a biological specimen and a hemoglobin-containing preservation solution that is capable of stably preserving hemoglobin.

In one aspect, the present disclosure relates to a method for stabilizing hemoglobin in a solution, and the method includes causing at least one of acetylacetone and uric acid to coexist in the hemoglobin-containing solution. In another aspect, the present disclosure relates to a method for stabilizing hemoglobin in a solution, includes preparing a hemoglobin solution by mixing hemoglobin as well as at least one of acetylacetone or uric acid, and preserving the hemoglobin solution for a certain period of time.

In another aspect, the present disclosure relates to a method for manufacturing a calibrator to be used for managing precision in testing hemoglobin in a biological specimen, the method includes preparing the calibrator by mixing hemoglobin as well as at least one of acetylacetone or uric acid.

In another aspect, the present disclosure relates to a method for measuring hemoglobin in a biological specimen, the method includes measuring hemoglobin in a pre-prepared hemoglobin solution as a control or calibrator for measuring hemoglobin, and measuring hemoglobin in the biological specimen. The hemoglobin solution is a hemoglobin solution that was prepared by mixing hemoglobin as well as at least one of acetylacetone or uric acid and has maintained a certain period of time after the preparation. In another aspect, the present disclosure relates to a method for measuring hemoglobin in a biological specimen, the method includes performing stabilization treatment for stabilizing hemoglobin in a hemoglobin solution, performing quality control of an analysis device or a reagent by using the hemoglobin solution having been subjected to the stabilization treatment and measuring hemoglobin in the biological specimen, using the analysis device or the reagent having been subjected to the quality control. The stabilization treatment for stabilizing hemoglobin includes mixing hemoglobin, acetylacetone, and uric acid.

In another aspect, the present disclosure relates to use of a hemoglobin solution for measuring hemoglobin in a biological specimen, the use including measuring hemoglobin in a hemoglobin solution as a control or calibrator for measuring hemoglobin, and measuring hemoglobin in the biological specimen, wherein the hemoglobin solution is a hemoglobin solution that was prepared by mixing hemoglobin as well as at least one of acetylacetone and uric acid and has passed a certain period of time after the preparation.

In another aspect, the present disclosure relates to a hemoglobin-containing preservation solution that is a preservation solution containing hemoglobin as well as at least one of acetylacetone and uric acid.

With the present disclosure, in one aspect, a method that is capable of stably preserving hemoglobin in a solution, use of a hemoglobin solution for a method for measuring hemoglobin in a biological specimen and a hemoglobin-containing preservation solution are provided.

DETAILED DESCRIPTION

Figure 1:
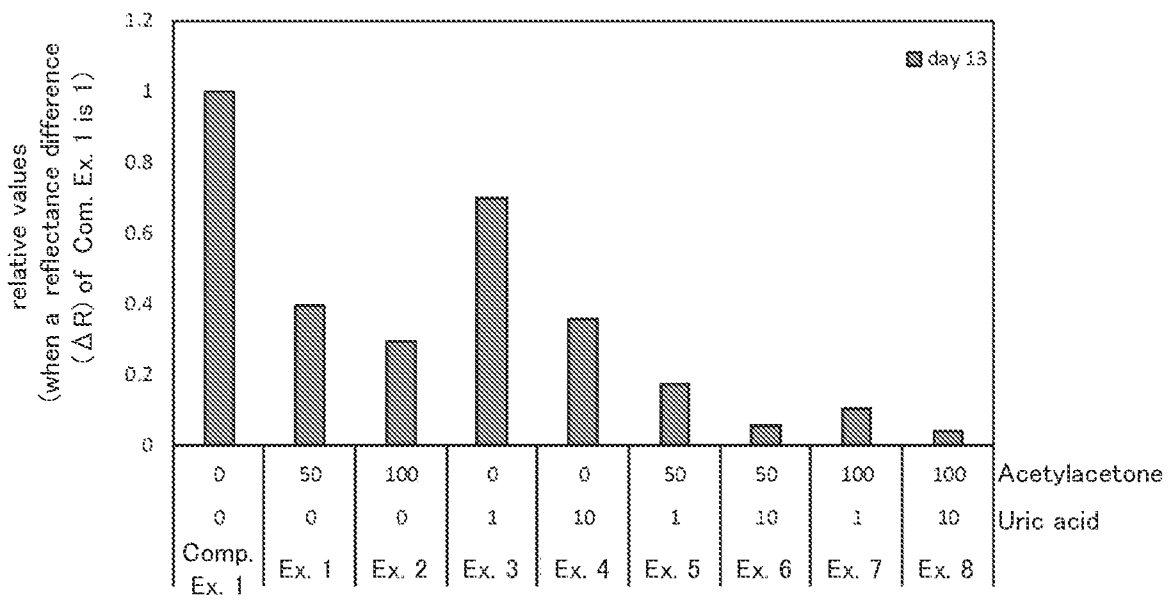
FIG. 1 is a graph illustrating exemplary results of a hemoglobin stability confirmation test of preserving hemoglobin in a solution at 30° C. for 13 days.

As a measuring method used in laboratory testing, the following are available, A method performed by mixing a liquid reagent and a biological specimen; and a method using a dry-type test strip that is obtained by impregnating filter paper or the like with a reagent and drying the same. Measurement using a test strip is widely performed as a screening test, because the method is easy to operate, and the method is capable of measuring a plurality of items simultaneously. Quality control using a control reagent is performed at least once a day, though the frequency varies depending on the facility performing the laboratory testing. As a control reagent, liquid-type control reagents, and lyophilized powder-type control reagents prepared at the time of use are available.

In the case of the lyophilized powder-type control reagent, which has to be prepared at the time of use, the complexity of the operation is problematic. In the case of the liquid-type control reagent, it is necessary to stably preserve components (for example, items to be measured) contained in the control reagent.

One of the items to be measured in a biological specimen such as urine, feces, blood, or saliva is hemoglobin (occult blood, BLD). A control reagent containing hemoglobin is therefore used. Hemoglobin, however, has low preservation stability in solution. For example, hemoglobin may be denatured depending on the preservation conditions such as preservation temperature, and may be decomposed in some cases. As a result, the three-dimensional structure of hemoglobin may be destroyed in some cases, which can cause a problem as the control reagent does not function properly for quality control purpose.

Accordingly, the present disclosure provides a method capable of preserving hemoglobin stably in a solution containing hemoglobin, for example, a reagent solution for quality control used for controlling the quality of laboratory testing on a biological specimen. In one or a plurality of embodiments, exemplary a laboratory testing on a biological specimen in the present disclosure includes urine testing, blood testing, feces testing and saliva testing. Examples of the biological specimen, in one or a plurality of embodiments, include urine, feces, blood, saliva, and specimens derived from these. Examples of the biological specimen, in one or a plurality of embodiments, include specimens derived from humans, and specimens derived from animals other than humans.

The present inventor has found that by causing at least either one of acetylacetone and uric acid to coexist in a hemoglobin-containing solution, the preservation stability of hemoglobin in the solution can be improved. With the present disclosure, in one or a plurality of embodiments, hemoglobin (for example, human hemoglobin) can be stably preserved in a solution.

Uric acid is a weak organic acid (pKa: 5.75). About 98% of the uric acid is found to be in the dissociated form (urate) at physiological pH (7.40), and when the pH is less than 5.75, the non-dissociated form (uric acid) is predominant. The "uric acid" in the present disclosure, encompasses uric acid and urate.

The "hemoglobin-containing solution (hemoglobin solution)" in the present disclosure, in one or a plurality of embodiments, refers to a solution containing hemoglobin at a concentration of 0.06 mg/dL (0,0006 mg/mL) to 2.0 mg/dl, (0.02 mg/mL). In one or a plurality of embodiments, the concentration of hemoglobin in the solution may be 0.1 mg/dL (0.001 mg/mL) or more, 0.5 mg/dL (0.005 mg/mL) or more, 0.7 mg/dL (0.007 mg/mL) or more, 0.8 mg/dL (0.008 mg/mL) or more. 0.9 mg/dL (0.009 mg/mL) or more, or 1 mg/dL (0.01 mg/mL) or more. The concentration of hemoglobin in the solution, in one or a plurality of embodiments, may be 2 mg/dL (0.02 mg/mL) or less, 1.9 mg/dL (0.019 mg/mL) or less, 1.8 mg/dL (0.018 trig/mL) or less, or 1.7 mg/dL (0.017 mg/mL) or less. The concentration of hemoglobin may be a range comprising end points as set out above, for example having a range of 0.1 mg/dL (0.001 mg/mL) to 1.7 mg/dL (0.017 mg/mL). The concentration of hemoglobin in the solution, in one or a plurality of embodiments, can be measured by measurement of the pseudoperoxidase activity in hemoglobin, the cyanmethemoglobin method, an immunological detection method utilizing a hemoglobin antibody, or the like.

In the present disclosure, in one or a plurality of embodiments, "being capable of stably preserving hemoglobin" refers to, for example, that maintenance of peroxidase (POD) activity of hemoglobin. This may be used to define hemoglobin that has been stably preserved. In one or a plurality of embodiments, the POD activity of hemoglobin can be confirmed by measuring reflectance of a BLD pad of the test strip (at a wavelength of 570 to 660 nm). The BLD pad of a test strip, in one or a plurality of embodiments, includes a BLD pad of urine test strip such as AUTION Sticks 10 PA (product name, manufactured by Arkray Inc).

In the present disclosure, in one or a plurality of embodiments, "being capable of stably preserving hemoglobin" refers to, for example, that the difference (the absolute value of a difference) between the value of hemoglobin measured immediately after the preparation of a hemoglobin-containing solution and the value of hemoglobin measured after preservation (e.g. maintenance) of the solution ([value after preservation]−[value immediately after preparation]) is small. In one or a plurality of embodiments, an exemplary measured value of hemoglobin is the reflectance (at a wavelength of 570 to 660 nm) of a BLD pad of a urine test strip. In the present disclosure, "immediately after preparation" means a timing within 60 minutes after at least either one of acetylacetone and uric acid is added to a hemoglobin-containing solution (after both acetylacetone and uric acid are added in the case where acetylacetone and uric acid are mixed).

In one or a plurality of embodiments, "being capable of stably preserving hemoglobin" refers to, for example, that, regarding the reflectance (at a wavelength of 570 to 660 nm) of a BLD pad of a urine test strip, the difference ($\Delta R=R_{aft13}-R_{bef}$) between the reflectance $R_{bef}$ and the reflectance $R_{aft13}$ is 50 or less, 45 or less, 25 or less, 20 or less, 15 or less, 10 or less, 8 or less, 7 or less, 5 or less, or 4 or less. The reflectance $R_{bef}$ means the reflectance measured immediately after the preparation of the hemoglobin-containing solution. The reflectance $R_{aft13}$ means the reflectance measured after preservation of the solution at 30° C. for 13 days.

In one or a plurality of embodiments, "being capable of stably preserving hemoglobin" refers to, for example, that, regarding the reflectance (at a wavelength of 570 to 660 nm) of a BLD pad of a urine test strip, the difference ($\Delta R=R_{aft27}-R_{bef}$) between the reflectance $R_{bef}$ immediately after the preparation of the hemoglobin-containing solution and the reflectance $R_{aft27}$ after preservation of the solution at 30° C. for 27 days is 80 or less, 70 or less, 55 or less, 50 or less, 45 or less, 40 or less, 35 or less, or 30 or less. The reflectance $R_{bef}$ is as above. The reflectance $R_{aft27}$ means the reflectance measured after preservation of the solution at 30° C. for 27 days.

The reflectance can be measured by a method described in Examples,

[Stabilization Method]

In one aspect, the present disclosure relates to a method for stabilizing hemoglobin in a solution, and the method includes causing at least either one of acetylacetone and uric acid to coexist in the hemoglobin-containing solution (this method is also hereinafter referred to as "the method of the present disclosure"). The method of the present disclosure, in one or a plurality of embodiments, can be suitably used for improving the stabilization of hemoglobin in a reagent solution for quality control. The hemoglobin-containing solution in the present disclosure, therefore, is suitable for use as a reagent solution for quality control in one or a plurality of embodiments. In one or a plurality of embodiments, exemplary quality control reagent solutions in the present disclosure include a control reagent for urine testing, a control reagent for blood testing, a control reagent for feces testing, and a control reagent for saliva testing.

In one or a plurality of embodiments, from the viewpoint of further improving the stability of hemoglobin, the method of the present disclosure preferably includes causing both of acetylacetone and uric acid to coexist in the hemoglobin-containing solution.

In one or a plurality of embodiments, the concentration of acetylacetone in the solution is 10 mg/dL (0.1 mg/mL) to 200 mg/dL (2 mg/mL). From the viewpoint of further improving the stability of hemoglobin, the concentration of acetylacetone in the solution, in one or a plurality of embodiments, is 20 mg/dL (0.2 mg/mL) or more, 30 mg/dL (0.3 mg/mL) or more, 40 mg/dL (0.4 mg/mL) or more, 50 mg/dL (0.5 mg/mL) or more, 60 mg/dL (0.6 mg/mL) or more, 70 mg/dL (0.7 mg/mL) or more, 80 mg/dL (0.8 mg/mL) or more, 90 mg/dL (0.9 mg/mL) or more, or 100 mg/dL (1 mg/mL) or more. From the same viewpoint, in one or a plurality of embodiments, the concentration of acetylacetone in the solution is 190 mg/dL (1.9 mg/mL) or less, or 180 mg/dL (1.8 mg/mL) or less. The concentration of acetylacetone may be a range comprising end points as set out above, for example having a range of 20 mg/dL (0.2 mg/mL) to 180 mg/dL (1.8 mg/mL).

In one or a plurality of embodiments, the concentration of uric acid in the solution is 1 mg/dL (0.01 mg/mL) to 20 mg/dL (0.2 mg/mL). From the viewpoint of further improving the stability of hemoglobin, the concentration of uric acid in the solution, in one or a plurality of embodiments, is 2 mg/dL (0.02 mg/mL) or more; 3 mg/dL (0.03 mg/mL) or more, 4 mg/dL (0.04 mg/mL) or more; 5 mg/dL (0.05 mg/mL) or more. 6 mg/dL (0.06 mg/mL) or more, 7 mg/dL (0.07 mg/mL) or more, 8 mg/dL (0.08 mg/mL) or more, 9 mg/dL (0.09 mg/mL) or more, or 10 mg/dL (0.1 mg/mL) or more. From the same viewpoint, in one or a plurality of embodiments, the concentration of uric acid in the solution is 19 mg/dL (0.19 mg/mL) or less, or 18 mg/dL (0.18 mg/mL) or less. The concentration of uric acid may be a range comprising end points as set out above, for example having a range of 2 mg/dL (0.02 mg/mL) to 18 mg/dL (0.18 mg/mL).

The uric acid to be used in the method of the present disclosure may, in one or a plurality of embodiments, include monosodium urate.

In one or a plurality of embodiments, from the viewpoint of further improving the stability of hemoglobin, the method of the present disclosure preferably includes causing acetylacetone and uric acid to coexist in the hemoglobin-containing solution so that the concentration of acetylacetone in the solution is 10 mg/dL (0.1 mg/mL) to 200 mg/dL (2 mg/mL) and the concentration of uric acid in the solution is 1 mg/dL (0.01 mg/mL) to 20 mg/dL (0.2 mg/mL). The method of the present disclosure more preferably includes causing acetylacetone and uric acid to coexist therein so that the concentration of acetylacetone is 40 mg/dL (0.4 mg/mL) to 120 mg/dL (1.2 mg/mL) and the concentration of uric acid is 5 mg/dL (0.05 mg/mL) to 15 mg/dL (0.15 mg/mL). Other preferred uric acid and acetylacetone concentrations (as described hereinbefore) may also be combined. In one or a plurality of particularly non-limiting embodiments, the method of the present disclosure includes, for example, causing acetylacetone and uric acid to coexist in the hemoglobin-containing solution so that the concentration of acetylacetone is approximately 50 mg/dL (0.5 mg/mL) and the concentration of uric acid is approximately 10 mg/dL (0.1 mg/mL), or the concentration of acetylacetone is approximately 100 mg/dL (1 mg/mL) and the concentration of uric acid is approximately 10 mg/dL (0.1 mg/mL). For example, the concentration may vary by less than 10% or 5% relative to the indicated concentration.

With the method of the present disclosure, in one or a plurality of embodiments, hemoglobin can be preserved in a stable state in a solution at 8° C. for one month or more, and further, hemoglobin can be stably preserved in a solution at 8° C. for 6 months or more, 8 months or more, 10 months or more, or 12 months or more. By way of example, the hemoglobin may be preserved for up to 12, 24 or 26 months in this and other preservation conditions described herein. The method of the present disclosure, therefore, in one or a plurality of embodiments, includes preserving a solution containing hemoglobin as well as at least either one of acetylacetone and uric acid for a certain period of time. Alternatively expressed the method stably preserves hemoglobin in a solution, wherein stable preservation is as described hereinbefore, Examples of the preservation for a certain period of time in the method of the present disclosure, in one or a plurality of embodiments, include the preservation at 8° C. for 5 days or more, 10 days or more, 11 days or more, 12 days or more, 13 days or more, 14 days or more, 15 days or more, 16 days or more, 17 days or more, 18 days or more, 19 days or more, 20 days or more, 1 month or more, 6 month or more, 8 months or more, months or more, or 12 months or more.

With the method of the present disclosure, in one or a plurality of embodiments, hemoglobin can be preserved in a stable state in a solution at 30° C. for days or more, and further, hemoglobin can be preserved stably in a solution at 30° C. for 15 days or more, 20 days or more, or 25 days or more. With the method of the present disclosure, in one or a plurality of embodiments, hemoglobin can be preserved in a stable state in a solution at 20° C. for 1.5 months or more, and further, hemoglobin can be preserved stably in a solution at 20° C. for 2 months or more, 2.5 months or more, or 3 months or more. With the method of the present disclosure, in one or a plurality of embodiments, hemoglobin can be preserved in a stable state in a solution at 4° C. for 13 months or more, and further, hemoglobin can be preserved stably in a solution at 4° C. for 15 months or more, 20 months or more, 25 months or more, or 27 months or more.

Other aspects of the preservation for a certain period of time in the method of the present disclosure, in one or a plurality of embodiments, may include: the preservation at 30° C. for 5 days or more, 6 days or more, 7 days or more, 8 days or more, 9 days or more, 10 days or more, 15 days or more, 20 days or more, or 25 days or more; the preservation at 20° C. for 15 days or more, 1 month or more, 1.5 months or more, 2 months or more. 2.5 months or more, or 3 months or more; or the preservation at 4° C. for 1 month or more, 2 months or more, 3 months or more, 4 months or more, 6 months or more, 10 months or more, 12 months or more, 13 months or more, 15 months or more, 20 months or more, 25 months or more, or 27 months or more.

In the present disclosure, the preservation can encompass transport and/or storage. Thus, the preservation (i.e. stability of the hemoglobin) is maintained even during transport and/or storage.

The hemoglobin-containing solution, in one or a plurality of embodiments, may contain a buffer. In one or a plurality of embodiments, examples of the buffer include phosphoric acid, N,N-Bis(2-hydroxyethyl)glycine (Bicine), N,N-Bis(2-hydroxyethyl)-2-aminoethanesulfonic acid (BES), 3-Morpholinopropanesulfonic acid (MOPS), N-Tris(hydroxymethyl)methyl-2-aminoethanesulfonic acid (TES), 2-[4-(2-Hydroxy ethyl)-1-piperazinyl]ethanesulfonic acid (HEPES), N-[Tris(hydroxymethyl)methyl]glycine (TRICINE), Piperazine-1,4-bis(2-ethanesulfonic acid) (PIPES), and Piperazine-1,4-bis(2-hydroxy-3-propanesulfonic acid) dehydrate (POPSO).

In the present disclosure, the hemoglobin-containing solution, in one or a plurality of embodiments, does not contain biological urine, such as human urine.

In one or a plurality of embodiments, the hemoglobin-containing solution has a pH of 7 to 9. The value of pH of the hemoglobin-containing solution in the present disclosure, therefore, is a value at 25° C., which can be measured using a pH meter. More specifically, pH can be measured by a method described in Examples.

The hemoglobin-containing solution, in one or a plurality of embodiments, may contain a component other than hemoglobin, acetylacetone and/or uric acid. Examples of the other component, in one or a plurality of embodiments, include creatinine, glucose, albumin, elastase, glycine, methylchloroisothiazolinone, 2-methyl-4-isothiazolin-3-one, sodium azide, sodium nitrite, gentamicin sulfate, tobramycin, urea, sodium chloride, and potassium chloride. In one or a plurality of embodiments, examples of albumin include bovine serum albumin and human serum albumin.

An exemplary combination of the other components is a combination of sodium chloride, urea, creatinine, and potassium chloride. Another exemplary combination of components other than hemoglobin is a combination of creatinine, glucose, albumin, and elastase. In one or a plurality of embodiments, the formulation (hemoglobin-containing solution) containing such a combination as those described above can be used, not only as a hemoglobin control reagent, but also as a control reagent for glucose, protein, creatinine, nitrite, and/or leucocytes.

The hemoglobin-containing solution, in one or a plurality of embodiments, may contain a phosphoric acid buffer, as well as at least one, two, or more selected from the group consisting of creatinine, glucose, albumin, elastase, glycine, methylchloroisothiazolinon, 2-methyl-4-isothiazolin-3-one, sodium azide, sodium nitrite, gentamicin sulfate, tobramycin, urea, sodium chloride, potassium chloride, and the like.

[Preservation Solution]

The present disclosure relates to a preservation solution for preserving hemoglobin as another aspect. The preservation solution of the present disclosure contains hemoglobin as well as at least either one of acetylacetone and uric acid. In the present disclosure, the "hemoglobin preservation solution" refers to a solution containing hemoglobin in which the hemoglobin is (or will be) preserved in the solution, and in one or a plurality of embodiments, it refers to a hemoglobin-containing solution that can be used as a control or calibrator, and is intended for or capable of stably preserving hemoglobin. The hemoglobin preservation solution is also referred to as a hemoglobin-containing preservation solution herein.

The preservation solution of the present disclosure, in one or a plurality of embodiments, can be suitably used for improving the stabilization of hemoglobin in a control reagent such as a reagent solution for quality control. In one or a plurality of embodiments, the preservation solution of the present disclosure can be used as a control or calibrator, and preferably, it can be used as a control for urine testing, a blood testing, feces testing, or saliva testing.

The concentration of acetylacetone, the concentration of uric acid, the buffer, the pH, the other components, and the like in the preservation solution of the present disclosure are identical to those in the method of the present disclosure.

The preservation solution of the present disclosure in one or a plurality of embodiments can be produced by mixing hemoglobin and acetylacetone and/or uric acid, as well as optionally other components. The present disclosure, as another aspect, relates to a method for manufacturing a preservation solution for preserving hemoglobin, and the method includes mixing hemoglobin, acetylacetone and/or uric acid, as well as optionally the above-described other components. This provides a hemoglobin-containing preservation solution. The manufacturing method of the present disclosure, in one or a plurality of embodiments, includes adjusting acetylacetone and/or uric acid in the solution so that the concentration thereof falls in the above-described range. The manufacturing method of the present disclosure, in one or a plurality of embodiments, may include preserving (e.g. maintaining) the hemoglobin preservation solution that has been prepared by mixing hemoglobin, acetylacetone and/or uric acid, as well as optionally the other components, for a certain period of time. Such times are as previously described.

[Hemoglobin Testing Method]

The present disclosure, in another aspect, relates to a method for testing hemoglobin in a biological specimen, and the method includes measuring hemoglobin in a pre-prepared hemoglobin solution as a control or calibrator for measuring hemoglobin; and measuring hemoglobin in the biological specimen, wherein the pre-prepared hemoglobin solution is a solution containing hemoglobin that was prepared by mixing hemoglobin as well as at least either one of acetylacetone and uric acid and has been maintained for a certain period of time after the preparation. Such times are as previously described. In the method (or use as described hereinafter), the hemoglobin is measured in the biological specimen by reference to the pre-prepared hemoglobin solution (or hemoglobin solution) which acts as the control or calibrator. This allows accurate determination of the hemoglobin in the biological specimen.

The present disclosure, in another aspect, relates to use of a hemoglobin solution in a method for testing hemoglobin in a biological specimen. The use includes measuring hemoglobin in the hemoglobin solution as a control or calibrator for measuring hemoglobin; and measuring hemoglobin in the biological specimen, wherein the hemoglobin solution is a hemoglobin solution that was prepared by mixing hemoglobin as well as at least either one of acetylacetone and uric acid and has been maintained for a certain period of time after the preparation. Such times are as previously described. Also provided is use of a hemoglobin solution as described hereinbefore in a method for testing (e.g. measuring) hemoglobin in a biological specimen, in this use the hemoglobin solution is provided as a control or calibrator, i.e. further provided is use of a hemoglobin solution as described hereinbefore as a control or calibrator for testing/measuring (e.g. measuring the concentration of) hemoglobin in a biological specimen. The use may be performed in methods of testing/measuring hemoglobin and may include steps as described herein.

As the hemoglobin solution used in these aspects, a hemoglobin solution stably preserved by the method of the present disclosure can be used.

In the present disclosure, the method for testing or measuring hemoglobin in a biological specimen is not limited particularly, but in one or a plurality of embodiments, an example of the same is a method of optically analyzing a color exhibited after bringing a biological specimen or the hemoglobin solution used as a control or calibrator into contact with a detection reagent. The contact of a biological specimen and/or hemoglobin solution with a detection reagent, in one or a plurality of embodiments, can be performed by mixing the biological specimen or hemoglobin solution with the detection reagent, and supplying the biological specimen or hemoglobin solution to a test strip and/or a dry-type test strip for measuring hemoglobin.

Exemplary optical analysis, in one or a plurality of embodiments, is spectroscopic analysis that includes obtaining information relating to an analysis substance from transmitted light, reflected light, or scattered light of the analysis substance by using a spectroscope or the like. In one or a plurality of embodiments, as a result of optical analysis, the absorbance, transmittance, reflectance, or the like of hemoglobin at a desired wavelength is obtained. Exemplary optical analysis may be as follows: transmitted light, reflected light, or scattered light of a detection reagent brought into contact with a specimen is detected, and from the detected light, a value indicating an optical characteristic such as absorbance, transmittance, or reflectance of the detection reagent is calculated. However, the form of optical analysis is not limited to this. Optical analysis also encompasses measurement using other optical methods and/or spectroscopy.

Exemplary optical analysis of color, in one or a plurality of embodiments, is optical analysis of a mixed solution of the biological specimen or hemoglobin solution with a detection reagent, optical analysis of a reagent pad of a dry-type test strip for hemoglobin measurement, or the like. The optical analysis of color, however, does not have to be limited to these forms, and may be in a conventionally known form. In addition, in the present specification, the "color" can encompass color developed from a colorless state, and color resulting from transition from another color.

The optical analysis can be performed by using a commercially available optical analysis device. In one or a plurality of embodiments, examples of the optical analysis device include AUTION MAX (registered trademark) (manufactured by Arkray Inc.).

The present disclosure may relate to one or a plurality of non-limiting embodiments described below.

[A1] A method for stabilizing hemoglobin in a solution, including causing at least one of acetylacetone or uric acid to coexist in the solution containing hemoglobin.

[A2] The method according to [A1], wherein the solution is a reagent solution for quality control.

[A3] The method according to [A1] or [A2], wherein the concentration of acetylacetone in the solution is 10 mg/dL to 200 mg/dL.

[A4] The method according to any one of [A1] to [A3], wherein the concentration of uric acid in the solution is 1 mg/dL to 20 mg/dL.

[A5] The method according to any one of [A1] to [A4], including causing acetylacetone and uric acid to coexist in the solution.

[A6] The method according to any one of [A1] to [A5], wherein the concentration of acetylacetone in the solution is 10 mg/dL to 200 mg/dL, and/or the concentration of uric acid in the solution is 1 mg/dL to 20 mg/dL.

[A7] The method according to any one of [A1] to [A6], wherein the solution further contains a phosphoric acid buffer.

[A8] The method according to any one of [A1] to [A7], wherein the solution has a pH of 7 to 9.

[A9] The method according to any one of [A1] to [A8], including preserving (e.g. maintaining) the solution containing hemoglobin as well as at least one of acetylacetone or uric acid for a certain period of time.

[A10] The method according to any one of [A1] to [A9], wherein the solution further contains at least one selected from the group consisting of creatinine, glucose, albumin, elastase, and sodium nitrite.

[A11] The method according to any one of [A1] to [A10], wherein the solution does not contain human urine.

[A12] A hemoglobin preservation solution containing hemoglobin; and at least one of acetylacetone or uric acid.

[A13] The preservation solution according to [A12], wherein the preservation solution is a reagent solution for quality control.

[A14] The preservation solution according to [A12] or [A13], containing hemoglobin, acetylacetone, and uric acid.

[A15] The preservation solution according to any one of [A12] to [A14], wherein the concentration of acetylacetone in the solution is 10 mg/dL to 200 mg/dL.

[A16] The preservation solution according to any one of [A12] to [A15], wherein the concentration of uric acid in the solution is 1 mg/dL to 20 mg/dL.

[A17] The preservation solution according to any one of [A12] to [A16], wherein the concentration of acetylacetone in the solution is 10 mg/dL to 200 mg/dL, and/or the concentration of uric acid in the solution is 1 mg/dL to 20 mg/dL.

[A18] The preservation solution according to any one of [A12] to [A17], wherein the preservation solution further contains a phosphoric acid buffer, and/or at least one selected from the group consisting of creatinine, glucose, albumin, elastase, and sodium nitrite.

[A19] The preservation solution according to any one of [A12] to [A18], to be used as a control for a urine test. Such a solution is suitable for, or for use as, a control for this purpose.

[B1] A method for stabilizing hemoglobin in a solution, including preparing a hemoglobin solution by mixing hemoglobin as well as at least one of acetylacetone or uric acid; and preserving the hemoglobin solution for a certain period of time.

[B2] The method according to [B1], wherein the concentration of acetylacetone in the hemoglobin solution is 10 mg/dL to 200 mg/dL.

[B3] The method according to [B1] or [B2], wherein the concentration of uric acid in the hemoglobin solution is 1 mg/dL to 20 mg/dL.

[B4] The method according to any one of [B1] to [B3], wherein the hemoglobin solution contains hemoglobin, acetylacetone, and uric acid.

[B5] The method according to any one of [B1] to [B4], wherein the concentration of acetylacetone in the hemoglobin solution is 10 mg/dL to 200 mg/dL, and/or the concentration of uric acid in the hemoglobin solution is 1 mg/dL to 20 mg/dL.

[B6] The method according to any one of [B1] to [B5], wherein the hemoglobin solution further contains a phosphoric acid buffer.

[B7] The method according to any one of [B1] to [B6], therein the hemoglobin solution has a pH of 7 to 9.

[B8] The method according to any one of [B1] to [B7], further including shipping the hemoglobin solution to a remote location.

[B9] The method according to any one of [B1] to [B8], further including adding to the hemoglobin solution at least one selected from the group consisting of creatinine, glucose, albumin, elastase, and sodium nitrite.

[B10] The method according to any one of [B1] to [B9], wherein the hemoglobin solution does not contain human urine.

[B11] The method according to any one of [B1] to [B13], wherein the concentration of hemoglobin in the hemoglobin solution is 0.06 mg/dL to 2.0 mg/dL.

[B12] A method for manufacturing a calibrator to be used for managing precision in testing hemoglobin in a biological specimen, the method including preparing the calibrator by mixing hemoglobin as well as at least one of acetylacetone or uric acid. Such a calibrator is suitable for, or for use as, a calibrator for managing precision.

[B13] The method according to [B12], including mixing the acetylacetone and the hemoglobin so that the concentration of acetylacetone is 10 mg/dL to 200 mg/dL.

[B14] The method according to [B12] or [B13], including mixing the uric acid and the hemoglobin so that the concentration of uric acid is 1 mg/dL to 20 mg/dL.

[B15] The method according to any one of [B12] to [B14], including mixing the hemoglobin, the acetylacetone, and the uric acid so that the concentration of acetylacetone is 10 mg/dL to 200 mg/dL and the concentration of uric acid is 1 mg/dL to 20 mg/dL.

[B16] The method according to any one of [B12] to [B15], further including adding, in the calibrator a phosphoric acid buffer; and/or at least one selected from the group consisting of creatinine, glucose, albumin, elastase, and sodium nitrite.

[B17] The method according to any one of [B12] to [B16], including preserving the prepared calibrator for a certain period of time.

[B18] A method for measuring hemoglobin in a biological specimen, the method including measuring hemoglobin in a pre-prepared hemoglobin solution as a control or calibrator for measuring hemoglobin; and measuring hemoglobin in the biological specimen. The hemoglobin solution is a hemoglobin solution that was prepared by mixing hemoglobin as well as at least one of acetyl acetone or uric acid and has been maintained tier a certain period of time after the preparation.

[B19] A method for measuring hemoglobin in a biological specimen, the method including performing a stabilization treatment to stabilize hemoglobin in a hemoglobin solution; performing quality control of an analysis device or a reagent by using the hemoglobin solution which has been subjected to the stabilization treatment; and measuring hemoglobin in the biological specimen, using the analysis device or the reagent which has been subjected to the quality control. The stabilization treatment for stabilizing hemoglobin includes mixing hemoglobin, acetylacetone, and uric acid.

[B20] The method according to [B19], wherein the mixing includes mixing the hemoglobin, the acetylacetone, and the uric acid so that the concentration of acetylacetone is 10 mg/dL to 200 mg/dL, the concentration of uric acid is 1 mg/dL to 20 mg/dL, and the concentration of hemoglobin is 0.06 mg/dL to 2.0 mg/dL.

[C1] Use of a hemoglobin solution in a method for measuring hemoglobin in a biological specimen, the method including measuring hemoglobin in a pre-prepared hemoglobin solution as a control or calibrator for measuring hemoglobin; and measuring hemoglobin in the biological specimen. The hemoglobin solution is a hemoglobin solution that was prepared by mixing hemoglobin as well as at least one of acetylacetone or uric acid and has been maintained for a certain period of time after the preparation.

[C2] The use according to [C1], wherein the hemoglobin solution contains hemoglobin, acetylacetone, and uric acid.

[C3] The use according to [C1] or [C2], wherein the concentration of acetylacetone in the hemoglobin solution is 10 mg/dL to 200 mg/dL.

[C4] The use according to any one of [C1] to [C3], wherein the concentration of uric acid in the hemoglobin solution is 1 mg/dL to 20 mg/dL.

[C5] The use according to any one of [C1] to [C4], wherein the hemoglobin solution further contains: a phosphoric acid buffer; and/or at least one selected from the group consisting of creatinine, glucose, albumin, elastase, and sodium nitrite.

[C6] The use according to any one of [C1] to [C5], wherein the concentration of hemoglobin in the hemoglobin solution is 0.06 mg/dL to 2.0 mg/dL.

Hereinafter, although the following description describes the present disclosure in more detail by way of examples, these are illustrative, and the present disclosure is not limited to these examples.

EXAMPLE

[Preparation of Hemoglobin-Containing Solution]

A stock solution was prepared by combining the following components in the indicated amounts, and mixing the same with purified water so that the total amount was 100 mL, whereby a hemoglobin-containing solution having the composition shown in <Hemoglobin-containing solution> below was prepared. The concentrations of monosodium urate and acetylacetone in hemoglobin-containing solutions of the Examples and Comparative Examples were as shown in Tables 1 and 2 below.

<Stock Solution and Component Amounts>

125 mil phosphoric acid buffer solution 80 mL
5,000 mg/dL creatinine 4.4 mL
150 mg/dL monosodium urate 0 mL, 0.67 mL, or 6.7 mL
5,000 mg/dL glucose 0.8 mL
8,000 mg/dL BSA 2.5 mL
100 mg/dL human hemoglobin 1.5 mL
8,000 mg/dL acetylacetone 0 mL, 0.63 mL, or 0.25 mL
50 mg/dL sodium nitrite 0.8 mL
50 mg/dL elastase 0.8 mL <Hemoglobin-Containing Solution>

100 mM phosphoric acid buffer solution
220 mg/dL creatinine
0 mg/dL, 1 mg/dL, or 10 mg/dL monosodium urate
400 mg/dL glucose
200 mg/dL BSA
1.5 mg/dL human hemoglobin
0 mg/dL, 50 mg/dL, or 100 mg/dL acetylacetone
0.4 mg/dL sodium nitrite
0.4 mg/dL elastase
pH: 8

The pH is the pH of the hemoglobin-containing solution measured at 25° C. using a pH meter (manufactured by HORIBA, Ltd), which is a value obtained 1 minute after immersion of the electrode of the pH meter in the hemoglobin-containing solution to be measured.

[Tests for Confirming Stability]

Stability of the hemoglobin-containing solution prepared through the following procedure was confirmed.

(1) A hemoglobin-containing solution was prepared by mixing the stock solution as described above, and 30 minutes after mixing, urine test strips (product name: AUTION Sticks 10PA, manufactured by Arkray Inc.) were immersed in the hemoglobin-containing solution, and reflectances ($R_{bef}$) (%) (hemoglobin measured values) of BLD (occult blood) test pads thereof were measured by AUTION MAX AX-4060 (measurement wavelength: 635 nm) (N=6).

(2) In parallel with the measurement of step (1), the prepared hemoglobin-containing solution was preserved at 30° C., for 13 days or 27 days.

(3) After the preservation of step (2), the urine test strips were immersed in the hemoglobin-containing solution after preservation for 13 days, and reflectances ($R_{aft13}$) (%) of the BLD test pads thereof were measured in the same manner as that of step (1) (N=6). Also, the urine test strips were immersed in the hemoglobin-containing solution after preservation for 27 days, and reflectances ($R_{aft27}$) (%) of the BLD test pads thereof were measured in the same manner as that of step (1) (N=6).

(4) Each difference between reflectances as measurement results of steps (3) and (1) (ΔR=[Value after preservation (Reflectance of (3): $R_{aft13}$ or $R_{aft27}$)]−[Initial value (Reflectance of (1): $R_{bef}$)]) was calculated.

The results obtained are shown in Tables 1 and 2 below and in FIGS. 1 and 2.

Incidentally, the BLD test pad of the urine test strip used in the measurement utilizes the color change reaction of the test strip caused by the peroxidase (POD)-like activity (pseudoperoxidase) of hemoglobin. In the BLD test pad, cumyl hydroperoxide (CHP) as the peroxide, and 3,3',5,5'-tetramethylbenzidine (TMBZ), which is a chromogen, are present. When a specimen containing hemoglobin (Hb) is brought into contact with the BLD test pad, cumyl hydroperoxide in the test pad is decomposed due to the peroxidase (POD)-like activity of hemoglobin (M), and oxygen is generated. This oxygen oxidizes a reduced form of 3,3',5,5'-tetramethylbenzidine, changing the same into oxidized TMBZ (colored), thereby causing the same to generate color. Thus, in accordance with the Hb concentration in the specimen, the test pad is colored, which enables measurement of the Hb concentration in the specimen.

Preservation at 30° C. for 13 days or 27 days is considered to be equivalent to 6.5 months or 13.5 months, respectively, in the case of preservation at 8° C. (inference based on Arrhenius analysis).

TABLE 1

| | Acetylacetone (mg/dL) | Monosodium urate (mg/dL) | Reflectance difference (ΔR) (13 days at 30° C.) |
|---|---|---|---|
| Comp. Ex. 1 | 0 | 0 | 64.1 |
| Ex. 1 | 50 | 0 | 25.3 |
| Ex. 2 | 100 | 0 | 18.8 |
| Ex. 3 | 0 | 1 | 44.8 |
| Ex. 4 | 0 | 10 | 22.9 |
| Ex. 5 | 50 | 1 | 11.0 |
| Ex. 6 | 50 | 10 | 3.9 |
| Ex. 7 | 100 | 1 | 6.7 |
| Ex. 8 | 100 | 10 | 2.9 |

TABLE 2

| | Acetylacetone (mg/dL) | Monosodium urate (mg/dL) | Reflectance difference (ΔR) (27 days at 30° C.) |
|---|---|---|---|
| Comp. Ex. 2 | 0 | 0 | 90.3 |
| Ex. 9 | 50 | 1 | 54.5 |
| Ex. 10 | 50 | 10 | 29.5 |
| Ex. 11 | 100 | 1 | 50.5 |
| Ex. 12 | 100 | 10 | 22.0 |

Figure 2:
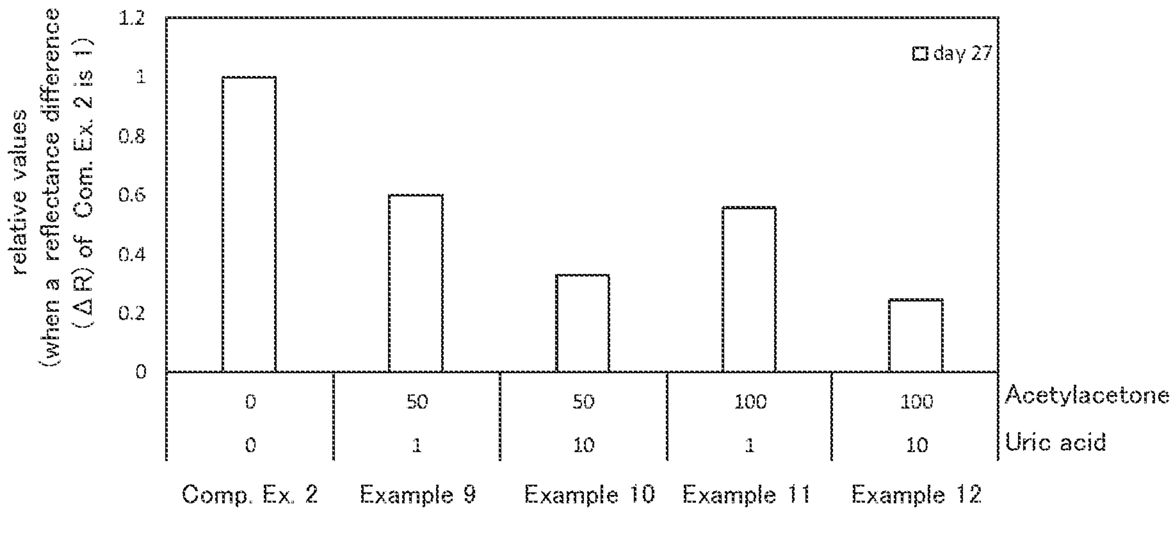
FIG. 2 is a graph illustrating exemplary results of a hemoglobin stability confirmation test of preserving hemoglobin in a solution at 30° C. for 27 days.

Table 1 and FIG. 1 show exemplary results of the stability confirmation test in the case of the 13-day preservation, and Table 2 and FIG. 2 show exemplary results of the stability confirmation test in the case of the 27-day preservation. FIG. 1 is a graph that shows relative values in the case where the reflectance difference (ΔR) in Comparative Example 1 (hemoglobin-containing solution that does not contain monosodium urate or acetylacetone) is assumed to be 1. FIG. 2 is a graph that shows relative values in a case where the reflectance difference (ΔR) in Comparative Example 2 (hemoglobin-containing solution that does not contain monosodium urate nor acetylacetone) is assumed to be 1.

As shown in Table 1, in the case of the 13-day preservation at 30° C., all of the reflectance differences (ΔR) from the initial values in Examples 1 to 8 (when acetylacetone and/or monosodium urate were present) were 50 or less, which makes it possible to consider that the POD activity of hemoglobin was maintained, and stable preservation was enabled.

As shown in FIG. 1, in the case of the 13-day preservation at 30° C., the relative values (change rates of reflectances) in Examples 1 to 8 (when acetylacetone and/or monosodium urate were present) were less than 0.7, which means that hemoglobin could be stably preserved in any of Examples. Among these, the relative values in Examples 5 to 8 in which both acetylacetone and monosodium urate were present were 0.17 or less, and particularly the relative values (change rates of reflectances) in Examples 6 and 8 in which acetylacetone and 10 mg/dL monosodium urate were present were 0.06 or less, which means that hemoglobin could be much more stably preserved.

As shown in Table 2, in the case of the 27-day preservation at 30° C., all of the reflectance differences (ΔR) from the initial values in Examples 9 to 12 (when acetylacetone and/or monosodium urate were present) were 55 or less, which makes it possible to consider that the POD activity of hemoglobin was maintained, and stable preservation was enabled.

As shown in FIG. 2, even in the case of the 27-day preservation at 30° C., all of the relative values (change rates) in Examples 9 to 12 were 0.6 or less, which means that hemoglobin could be stably preserved in any of Examples. Particularly, the relative values (change rates) in Examples 10 and 12 in which acetylacetone and 10 mg/dL monosodium urate were present were 0.33 or less. In other words, even in the case of the 27-day preservation at 30° C., as is the case with the 13-day preservation at 30° C., the presence of acetylacetone and/or monosodium urate allowed hemoglobin to be preserved stably.

The disclosure may be embodied in other forms without departing from the spirit or essential characteristics thereof. The embodiments disclosed in this application are to be considered in all respects as illustrative and not limiting. The scope of the disclosure is indicated by the appended claims rather than by the foregoing description, and all changes that come within the meaning and range of equivalency of the claims are intended to be embraced therein.

What is claimed is:

1. A method for stabilizing hemoglobin in a solution, including:

preparing a hemoglobin solution by mixing hemoglobin and acetylacetone; and preserving the hemoglobin solution for a certain period of time, wherein a concentration of acetylacetone in the hemoglobin solution is 0.1 mg/mL to 2 mg/mL.

2. The method according to claim 1, further comprising: adding uric acid to the hemoglobin solution.

3. The method according to claim 2, wherein a concentration of uric acid in the hemoglobin solution is 0.01 mg/mL to 0.2 mg/mL.

4. The method according to claim 1, wherein the hemoglobin solution includes hemoglobin, acetylacetone, and uric acid.

5. The method according to claim 1, wherein the hemoglobin solution further includes a phosphoric acid buffer.

6. The method according to a claim 1, further comprising: transporting the hemoglobin solution to a remote location.

7. The method according to claim 1, further comprising: adding to the hemoglobin solution at least one selected from the group consisting of creatinine, glucose, albumin, elastase, and sodium nitrite.

8. The method according to claim 1, wherein the hemoglobin solution is absent human urine.

9. The method according to claim 1, wherein a concentration of hemoglobin in the hemoglobin solution is 0.0006 mg/mL to 0.02 mg/mL.

10. The method according to claim 1, wherein the hemoglobin solution has a pH of 7 to 9.

11. A method for manufacturing a calibrator for managing precision in testing hemoglobin in a biological specimen, the method comprising:

preparing the calibrator by mixing hemoglobin and acetylacetone so that a concentration of acetylacetone is 0.1 mg/mL to 2 mg/mL.

12. The method according to claim 11, further comprising:

adding, in the calibrator, at least one of:

a phosphoric acid buffer; or at least one selected from the group consisting of creatinine, glucose, albumin, elastase, and sodium nitrite.

13. The method according to claim 11, further comprising:

preserving the calibrator for a certain period of time.

14. The method according to claim 11, wherein the hemoglobin solution has a pH of 7 to 9.

15. The method according to claim 11, wherein the preparing the calibrator includes mixing the hemoglobin, the acetylacetone, and a uric acid so that a concentration of acetylacetone is 0.1 mg/mL to 2 mg/mL, a concentration of uric acid is 0.01 mg/mL to 0.2 mg/mL.

16. A method for measuring hemoglobin in a biological specimen, the method comprising:

measuring hemoglobin in a pre-prepared hemoglobin solution as a control or calibrator for measuring hemoglobin; and measuring hemoglobin in a biological specimen, wherein the hemoglobin solution is a hemoglobin solution that was prepared by mixing hemoglobin and acetylacetone so that a concentration of acetylacetone is 0.1 mg/mL to 2 mg/mL and has maintained a certain period of time after the preparation.

17. The method according to claim 16, wherein the hemoglobin solution has a pH of 7 to 9.

18. A method for measuring hemoglobin in a biological specimen, the method comprising:

performing stabilization treatment for stabilizing hemoglobin in a hemoglobin solution;

performing quality control of an analysis device or a reagent by using the hemoglobin solution having been subjected to the stabilization treatment; and measuring hemoglobin in a biological specimen, using the analysis device or the reagent having been subjected to the quality control, wherein the stabilization treatment for stabilizing hemoglobin includes mixing hemoglobin, acetylacetone, and uric acid.

19. The method according to claim 18, wherein the mixing includes mixing the hemoglobin, the acetylacetone, and the uric acid so that a concentration of acetylacetone is 0.1 mg/mL to 2 mg/mL, a concentration of uric acid is 0.01 mg/mL to 0.2 mg/mL, and a concentration of hemoglobin is 0.0006 mg/mL to 0.02 mg/mL.

20. The method according to claim 18, wherein the hemoglobin solution has a pH of 7 to 9.

* * * * *